US006214337B1

(12) United States Patent
Hayen et al.

(10) Patent No.: US 6,214,337 B1
(45) Date of Patent: *Apr. 10, 2001

(54) ANIMAL FEEDS COMPRISING YEAST GLUCAN

(75) Inventors: Gary D. Hayen, Bartlesville, OK (US); Dennis Steven Pollmann, Fort Wayne, IN (US)

(73) Assignee: Biotec ASA, Tromso (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/136,784

(22) Filed: Aug. 19, 1998

Related U.S. Application Data

(62) Continuation of application No. 08/406,936, filed on Apr. 18, 1995, now abandoned, which is a continuation-in-part of application No. 08/102,935, filed as application No. PCT/US94/08152 on Jul. 20, 1994, now abandoned.

(51) Int. Cl.[7] .......................... A01N 63/00; A01N 63/04; A61K 31/715; A23C 9/12
(52) U.S. Cl. ............................ 424/93.51; 514/54; 426/62
(58) Field of Search ............................ 514/54; 424/93.51; 426/62

(56) References Cited

U.S. PATENT DOCUMENTS

| | | | |
|---|---|---|---|
| 3,856,940 | 12/1974 | Hamill et al. | 424/121 |
| 4,225,584 | 9/1980 | Hiller | 424/94 |
| 4,704,276 | 11/1987 | Kantor | 424/122 |
| 4,810,646 * | 3/1989 | Jamas et al. | 435/101 |
| 4,962,094 | 10/1990 | James et al. | 514/54 |
| 5,085,874 | 2/1992 | JungVid | 426/41 |
| 5,232,732 | 8/1993 | Harris et al. | 426/589 |
| 5,294,458 | 3/1994 | Fujimori | 426/635 |

FOREIGN PATENT DOCUMENTS 1153118   5/1969   (GB).

OTHER PUBLICATIONS

M.L. Salo et al, "Nutritive Value of Growing Pigs of Pekilo Protein and Torula Yeast Grown in Spent Sulphite Liquor", vol. 53, No. 1, 1981, pp. 52–56, Journal of the Scientific Agricultural Society of Finland.

* cited by examiner

Primary Examiner—Theodore J. Criares
(74) Attorney, Agent, or Firm—Ladas & Parry

(57) ABSTRACT

A composition and a process for enhancing animal growth by orally administering the animal with the composition are provided. The composition comprises an animal feed and a yeast glucan wherein the animal feed can contain at least one starch-bearing substance such as, for example, grain meal; at least one protein-bearing substance such as, for example, fish meal; a fat-containing substance such as, for example, soybean oil; and the yeast glucan can be obtained from a yeast such as, for example, *Saccharomyces cerevisiae*.

10 Claims, No Drawings

ANIMAL FEEDS COMPRISING YEAST GLUCAN

This application is a continuation of application Ser. No. 08/406,936 filed Apr. 18, 1995, now abandoned, which is a continuation-in-part of application Ser. No. 08/102,935 filed Aug. 6, 1993, now abandoned filed as PCT/US94/08152, Jul. 20, 1994.

FIELD OF THE INVENTION

This invention relates to an animal feed composition that comprises yeast glucan and a process for enhancing animal growth by feeding animals with the feed composition.

BACKGROUND OF THE INVENTION

Limited supply of conventional food protein is a major problem facing a rapid increase in world population. Of particular importance is the production of animal proteins that contain proteins having essential amino acids required by humans. Due to limited production facilities and lack of improvement in production technology, increase in animal protein production does not seem to proportionate the increase in world population.

Therefore, it appears highly desirable to improve the productivity of animal protein production. One of the means to improve the productivity is to develop feed compositions that enhance animal growth.

SUMMARY OF THE INVENTION

An object of the invention is to provide an animal feed composition. Another object of the invention is to provide a feed composition that would enhance animal growth. A further object of the invention is to provide a process for enhancing animal growth by feeding the animal with the feed composition. Other objects, features and advantages of the invention will become apparent as the invention is more fully disclosed hereinbelow.

According to a first embodiment of the invention, an animal feed composition that enhances animal growth is provided which comprises at least one starch-bearing substance, at least one protein-bearing substance, at least one fat-containing substance, and a yeast glucan.

According to a second embodiment of the invention, a process for enhancing animal growth is provided which comprises feeding a composition comprising at least one starch-bearing substance, at least one protein-bearing substance, at least one fat-containing substance, and a yeast glucan to an animal.

According to a third embodiment of the present invention, a composition is provided that can enhance the growth rate of an animal if the composition is orally administered to the animal. The composition comprises an animal feed and a yeast glucan. The yeast glucan is present in the composition in an amount sufficient to effect the growth enhancement.

According to a fourth embodiment of the present invention, a process for enhancing the growth of an animal is provided which comprises orally administering the composition which comprises an animal feed and a yeast glucan to an animal.

DETAILED DESCRIPTION OF THE INVENTION

According to the first embodiment of the present invention, any animals whose growth can be enhanced upon being fed with the composition of the invention can be employed in the present invention and can vary widely. The preferred animals are warm blood animals which include, but are not limited to, chickens, pigs, turkeys, and calves. The presently most preferred are newly weaned or hatched animals such as, for example, weanling pigs.

To enhance the growth, the length of time required for feeding the invention composition to the animal can vary widely depending on the type of animals. For example, for a weaning pig, it is preferred to feed it for about 7 to 40 days.

Suitable starch-bearing substances are those commonly used as feed components and are generally derived from grains selected from the group consisting of corn, soybean, wheat, sorghum, barley, oat, and mixtures thereof. Examples of suitable starch-bearing substances include, but are not limited to, corn flour, oat groat, ground corn, soybean flour, wheat flour, ground oat flour, wheat middlings, soybean meal, corn grit, and mixtures thereof. The presently preferred suitable starch-bearing substances are oat flour, ground corn, oat groat, wheat middlings, soybean meal, and mixtures thereof. These starch-bearing substances are commercially available.

A variety of protein-bearing substances can be used as a component of the invention composition as long as the protein-bearing substance can support the growth of an animal. The protein content of protein-bearing substances can vary over the range of from about 10 weight % to about 90%. For economical reasons, a crude protein-bearing substance such as, for example, a fish meal, dried whey, a soybean meal, and mixture thereof can be used. Other suitable protein-bearing substances include, but are not limited to, soybean protein concentrate, soy flour, blood meal, plasma protein, dried skim milk, whey protein concentrate, canola meal, corn gluten meal, wheat gluten meal, yeast, sunflower meal, and mixtures thereof. The presently preferred protein-bearing substances are fish meal, dried whey, blood meal, plasma protein and soybean meal. These protein-bearing substances are commercially available.

Any fat-containing substance that can support the growth of an animal can be used. Suitable fat-containing substances include, but are not limited to, lard, tallow, soybean oil, lecithin, coconut oil, whey-fat blend, and mixtures thereof. The presently preferred fat-containing substances are soybean oil, coconut oil, and lard.

The term "yeast glucan" is used in this application to refer generically, unless otherwise indicated, to an insoluble yeast cell wall material substantially free of mannan and phosphomannan or mannoprotein and has essentially no inherent nutritional value at the levels incorporated in the composition of the invention. Yeast glucan is mainly composed of a backbone chain of β(1–3) linked glucose units with a low degree of inter- and intra-molecular branching through β(1–6) linkages. A minor component that consists mainly of a highly branched β(1–6) linked glucan is closely associated with the main component and both comprise alkali-insoluble glucan fractions.

The yeast glucan used in the invention can contain a glucan content (β(1–3) and β(1–6) linkages measured as glucose) from about 40% to about 99%, a protein content from about 0.01% to about 50%, a lipid content from about 0.01 to about 50%, an ash content from about 0.01% to about 12%, and a solids content from about 10% to about 100%; preferably a glucan content from about 40% to about 90%, a protein content from about 0.05% to about 30%, a lipid content from about 0.05% to about 45%, an ash content from about 0.05% to about 10%, and a solids content from about 20% to about 99%; more preferably a glucan content from about 50% to about 90%, a protein content from about 0.1% to about 10%, a lipid content from about 0.1% to about 40%, an ash content from about 0.5% to about 8%, and a solids content from about 70% to about 98%; and most preferably a glucan content from 60% to 85%, a protein content from 1% to 8%, a lipid content from 1% to 35%, an ash content from 1% to 5%, and a solids content from 90% to 99%. The percentage disclosed in this application is weight percent.

The yeast glucan suitable for use in the invention can be derived from any yeast species. Preferably the yeast glucan is derived from a yeast selected from the group consisting of *Saccharomyces cerevisiae, Saccharomyces uvarum, Candida utilis, Kluyvecomyces fragilis, Pichia pastoris*, and combinations thereof. The presently preferred yeast species are *Saccharomyces cerevisiae* and *Candida utilis* because both have been traditionally and are used for food and feed supplements.

Yeast glucan can be prepared from the above-described yeast by any known method in the art including, for example, treatment with heat, bases, acids, enzymes, solvents, or combinations thereof. The choice of a suitable method is generally a matter of preference to those skilled in the art.

The presently preferred process for the preparation of a yeast glucan comprises: (1) preparing a yeast suspension in an alkaline solution to form a mixture containing an insoluble yeast cell wall fraction; (2) separating the insoluble yeast cell wall fraction from the mixture; (3) suspending the insoluble yeast cell wall fraction in an acid solution to form a yeast glucan; and (4) separating the yeast glucan.

The term "yeast suspension" used herein refers to, unless otherwise indicated, a liquid suspension of live yeast, inactive yeast, dried yeast, or combinations of two or more thereof.

According to the present invention, the yeast glucan can be prepared from a live yeast culture that is freshly grown, a yeast culture having a portion thereof that has lost viability (i.e., inactive yeast) a dried yeast, or combinations of two or more thereof. Processes for growing yeast or producing dried yeast are well known to those skilled in the art and are omitted here for the interest of brevity. A crude yeast glucan can also be prepared by any method known in the art including, for example, treatment with heat, bases, acids, enzymes, solvents, or combinations of two or more thereof. The choice of a suitable method for preparing the crude yeast glucan is generally a matter of preference to those skilled in the art.

Generally, a suspension of a yeast described above is prepared by addition of water to a concentration of from about 20 g/l to about 200 g/l, preferably from about 80 g/l to about 180 g/l, and most preferably from 100 g/l to 160 g/l. A basic compound in a solution then added to the suspension. The suspension can be mixed with any suitable means such as, for example, mechanical stirring with an agitator, to ensure a thorough distribution of the basic compound in the suspension. Alternatively, the yeast suspension can be added to the basic compound.

The basic compound used in the invention can be an organic base or an inorganic base and can be in either an aqueous or non-aqueous form. Generally the basic compound is substantially soluble in the suspension described above. The presently preferred basic compound is an inorganic base. Examples of suitable basic compounds include, but are not limited to, tetramethylammonium hydroxide, potassium hydroxide, sodium hydroxide, lithium hydroxide, magnesium hydroxide, calcium hydroxide, ammonium hydroxide, lithium carbonate, sodium carbonate, potassium carbonate, calcium carbonate, magnesium carbonate, and mixtures of two or more thereof. The presently most preferred basic compound is sodium hydroxide because of its availability and ease of use.

The amount of the basic compound required can vary widely, depending on the type of yeast or crude yeast glucan used. Generally, the basic compound is added to the above-described suspension such that the final concentration of the basic compound in the suspension is from about 0.01 M to about 6 M, preferably from about 0.1 M to about 3 M, and most preferably from 0.1 M to 2 M.

The mixture thus formed, containing the suspension, and the basic compound, is then subject to a treatment at a temperature of from about 20° C. to about 120° C. and preferably from about 20° C. to about 100° C. The time required for carrying out the process is generally in the range of from about ¼ hours to about 24 hours and most preferably from ½ hour to 20 hours. The process of the invention can be carried out in a wide range of pressure from about 0.1 atmospheres (atm) to about 10 atm, preferably from about 0.5 atm to about 5 atm, and most preferably from 1 atm to 2 atm.

After the above-described treatment, a mixture containing an insoluble yeast cell wall fraction is formed. The insoluble fraction is separated from the soluble fraction by a separation means known to one skilled in the art such as, for example, centrifugation followed by, if desired, washing with water.

The insoluble cell wall fraction is then acidified with an acid. Any acid can be used. Presently, the preferred acid is a mild acid such as, for example, acetic acid. The insoluble cell wall fraction can be suspended in water followed by addition of an acid or suspended directly in an acid. The amount of acid required is the amount that is required to adjust the pH of the cell wall fraction to about pH7 or lower. The treatment of acid can be carried out under the same conditions as described above for the alkaline treatment. After the acid treatment, a yeast glucan is prepared.

The yeast glucan can be recovered by any suitable conventional means known to one skilled in the art such as, for example, centrifugation, filtration, decantation, and combinations thereof. The yeast glucan recovered can be further washed with a washing agent selected from the group consisting of water, acetone, methanol, ethanol, aqueous sodium chloride solution, diluted acetic acid solution, ether, hexane, and combinations of two or more thereof. The yeast glucan recovered can be resuspended in water or dried for use. Any conventional drying means such as, for example, spray drying, drum drying, freeze drying, air drying, and combinations thereof can be used to dry the yeast glucan product.

The composition of the invention can also comprise water- and fat-soluble vitamins and trace minerals. Suitable vitamins include vitamin A, vitamin D, vitamin E, vitamin K, riboflavin, pantothenic acid, niacin, vitamin $B_{12}$, folic acid, biotin, vitamin C, and mixtures thereof. Suitable trace elements include copper, zinc, iodine, selenium, manganese, iron, cobalt, compounds thereof, or mixtures thereof. The term "trace" used herein denotes the quantity of these components used in the composition that is substantially smaller than that of other components. Generally the vitamins-trace minerals are present in the composition in the range of from about 0.0001 to about 5% based on total weight % of the composition.

According to the present invention, the composition can also contain an antioxidant such as, for example, ethoxyquin, BHT, BHA, vitamin E, ascorbic acid, and mixtures thereof. The composition can also contain an antibiotic mix such as, for example, chlorotetracycline, sulfamethazine, penicillin, and mixtures thereof. Generally very small quantity i.e., in the range of from about 0.0001 to about 1 weight %, of antioxidant or antibiotic is present in the composition.

The starch-bearing substance can be present in the composition in any concentration so long as it can effectively support the growth of an animal. The starch-bearing substance can be generally present in the composition in the range of from about 10 weight % to about 80 weight %, preferably about 15 weight % to about 50 weight %, and most preferably 20 weight % to 40 weight %.

Any concentration of protein-bearing substance can be employed as long as that concentration can effectively support the growth of an animal. Generally, the protein-bearing substance can be present in the composition in the range of from about 10 weight % to about 50 weight %, preferably about 15 weight % to about 40 weight %, and most preferably from 18 weight % to 30 weight %.

Similarly, any concentration of the fat-containing substance can be employed in the invention so long as that concentration can support the growth of the animal. The fat-containing substance generally can be present in the composition in the range of from about 2 weight % to about 20 weight %, preferably from about 4 weight % to about 15 weight %, and most preferably 6 weight % to 12 weight %.

The amount of the yeast glucan required in the composition is the amount that is required to increase the growth rate of an animal in the range of at least about 2%, preferably 4%, and most preferably 6%. The weight % of the yeast glucan present in the composition can generally be in the range of from about 0.001% to about 10%, preferably from about 0.01% to about 5%, and most preferably from 0.02% to 2%. The weight % of the vitamin-mineral mix described above can be present in the invention composition in the range of from about 0.0001% to about 5%, preferably about 0.001% to about 3%, and most preferably 0.01% to 2%.

All weight % disclosed herein is based on the total weight % of the composition equaling 100%.

In a preferred embodiment, in animal feed composition comprises 0.001% to 30% ground oat flour, 0.001% to 30% oat groats, 0.001% to 70% ground corn, 0.001% to 15% fish meal, 0.001% to 40% soybean meal, 0.001% to 8% ground soybean hulls, 0.001% to 40% dried whey, 0.1% to 40% wheat middlings, 0.001% to 30% whey-fat blend, 0.001% to 5% dicalcium phosphate, 0.001% to 4% calcium carbonate, 0.001% to 4% fumaric acid, 0.001% to 3% antibiotic mix, 0.001% to 1% butter, 0.001% to 1% maple flavor, 0.001% to 1% lysine HCl, and 0.001% to 2% vitamin-mineral mix; wherein the % is weight % based on total weight % of said composition being 100%; the antibiotic mix comprises 100 g of chlorotetracycline, 100 g of sulfamethazine, and 50 g of penicillin per ton of said composition; and the vitamin-mineral mix comprises copper sulfide, choline, selenium, vitamin E, biotin, folic acid, glycine, and ethoxyquin.

The composition is further illustrated in the feed diets disclosed in the Examples.

The composition of the first embodiment of the invention can be prepared by any mixing means known to one skilled in the art such as, for example, mechanical blending, extrusion, pelletizing, and spray drying. The order of adding individual components for mixing generally does not alter the physical characteristics or feeding efficiency of the composition. However, it is preferred that the yeast glucan be mixed with a carrier such as, for example, rice bran, grain, wheat bran, calcium carbonate, or mixtures thereof to facilitate even mixing and distribution. Any physical form of the composition such as, for example, powder, pellet, cube, semi-solid, and combinations thereof can be used.

According to the second embodiment of the invention, a process for enhancing animal growth is provided wherein the process comprises feeding an animal with an animal feed composition. The scope and preparation of the animal feed composition are the same as those described above in the first embodiment of the invention. The method for feeding the composition to animals are well known to one ordinarily skilled in the art. The choice of a specific delivery means is generally the preference of one skilled in the art. Specific methods for delivering the composition to animals are omitted for the interest of brevity.

According to the third embodiment of the present invention, a composition is provided which can be used to increase the growth rate of an animal by orally administering the composition to the animal. Any animal whose growth rate can be increased by at least about 2%, preferably about 4%, and most preferably 6%, upon being fed with the composition are suitable animals. Examples of such animals are the same as those disclosed in the first embodiment of the present invention.

According to the third embodiment of the present invention, any animal feed known to one skilled in the art or commercially available can be used in the present invention. Examples of suitable animal feeds generally contains a carbohydrate-containing substance, a protein-containing substance, and a lipid-containing substance; the scope and weight percent of which are the same as those disclosed above in the first embodiment of the present invention. A suitable animal feed can also contain water- and fat-soluble vitamins and trace minerals as well as antioxidant, scope and weight percent of these components are the same as those disclosed in the first embodiment of the invention.

The definition and scope of the yeast glucan are the same as those earlier disclosed in the first embodiment of the invention.

The concentration or amount of the yeast glucan in the composition is that concentration or amount that is sufficient to achieve a growth rate increase of at least about 2%, preferably about 4%, and most preferably 6% when an animal is fed with the composition. The presently preferred concentration is in the range of about 50 g to about 2,500 g, preferably about 100 g to about 2,000 g, and most preferably 200 g to 1,500 g of the yeast glucan per ton of the composition. The illustrative amount of the yeast glucan required to achieve the growth rate described above can also be expressed as unit weight per animal per day such as, for example, about 100 mg to 450 mg, preferably about 150 mg to about 400 mg, and most preferably 200 mg to 350 mg of yeast glucan per weanling pig per day.

The composition of the third embodiment of the present invention can be prepared by the same manner disclosed above in the first embodiment of the invention.

According to the fourth embodiment of the present invention, a process for enhancing the growth rate of an animal is provided which comprises orally administering an animal with a composition comprising an animal feed and a yeast glucan. The animal and the composition are the same as those disclosed above in the third embodiment of the invention. The time required to achieve the growth rate is the same as that disclosed in the second embodiment of the invention.

The following specific examples are provided to assist the understanding of the present invention and are not to be construed to unduly limit the scope of the invention.

Example I

This example provides a general protocol used to obtain a yeast glucan suitable for the practice of the present invention.

Dry *Saccharomyces cerevisiae* (500 g) was suspended in 3 liters of 6% aqueous NaOH solution. This suspension was then stirred overnight at room temperature. The suspension was then centrifuged at 2000×g for 25 minutes. The supernatant was discarded and the insoluble residue was resuspended in 3 liters of 3% NaOH and incubated for 3 hours at 75° C. followed by cooling the suspension overnight. The suspension was then centrifuged at 2000×g for 25 minutes and the supernatant was decanted.

The insoluble residue remaining was then adjusted to pH 4.5 with acetic acid. The insoluble residue was then washed with 2 liters of water three times and recovered by centrifuging at 2000×g for 25 minutes after each wash (the supernatant was poured off). The residue was then suspended in 3 liters of a 0.5 M aqueous acetic acid. The suspension was heated for 3 hours at 90° C. The suspension was then cooled to room temperature. The insoluble residue was then collected by centrifuging at 2000×g for 25 minutes.

The insoluble residue was then suspended in 3 liters of distilled water and stirred for 30 minutes at 100° C., then cooled and centrifuged at 2000×g for 25 minutes. The supernatant was discarded. The insoluble residue was spray dried and used in the following examples.

Example II

This example illustrates the effect of yeast glucan ($\beta$, 1–3 and 1–6 linkages) on enhancing growth of starter pigs.

A randomized, complete-block experiment was designed to feed the invention composition to starter pig. The yeast glucan employed in this Example was obtained by the process described in Example I and had about 60 weight % glucan (measured as glucose unit), about 6% protein, about 14% lipids, about 9% ash, and about 8% moisture. Six levels of yeast glucan were fed in Stage I and II (0.0, 0.5, 1.0, 1.5, 2.0 and 2.5 lbs/ton; the level expressed as 0.0 lb/ton was control diet). Four or five weanling pigs (19–21 days of age) were placed in each pen and each dietary treatment was represented by six weight replicates. Diets were based on current high performance diet standards (Table I).

Stage I diets (Table I) were fed to weanling pigs from day 0 to 13 and were based on 1.25% available lysine, 3300 kcal ME/kg of diet and formulated to contain 16% edible dried whey, 5% select menhaden fish meal, 10% oat flour and 10% oat groats.

Stage II diets were fed from day 14 to the end of the experiment (33 days) and were based on 1.15% available lysine, 3200 kcal ME/kg of diet and formulated to contain 6% edible dried whey, 3% select menhaden fish meal and 10% oat flour. Comparisons of feeding results were established using least-square means end linear, quadratic and cubic contrasts were tested in the statistical model. Pigs were weighed seven and thirteen days after the initiation of the experiment to better determine the effect of yeast glucan additions in Stage I growth.

The diet formulations are shown in Table I.

TABLE I

| Diet Composition for Starter Pigs | | |
|---|---|---|
| Ingredient | HSP 121–126[a] | HSP 127–132[b] |
| Ground Corn | 27.86 | 43.10 |
| Oat Flour | 10.00 | 10.00 |
| Rolled Oat Groats | 10.00 | — |
| Edible Dried Whey | 11.33 | 6.00 |
| Soybean Meal | 21.87 | 21.99 |
| Select Menhaden Fish Meal | 5.00 | 3.00 |
| 7/40 Whey-Fat Blend | 7.79 | — |
| Soybean Hulls | 1.68 | — |
| Standard Midds | — | 10.00 |
| Choice White Grease | — | 2.33 |
| Dicalcium Phosphate (18.5%) | .83 | 1.08 |
| Calcium Carbonate | .63 | .72 |
| Salt | — | .19 |
| Fumaric Acid | 1.25 | — |
| L-Lysine HCl | .11 | .19 |
| ASP-250 Premix[c] | .50 | .50 |
| CS-Butter | .30 | .20 |
| Corn Dextrose[d] | .25 | .25 |
| Other[e] | .60 | .45 |
| Calculated Nutrient Analysis | | |
| Crude Protein, % | 21.00 | 19.85 |
| Fat, % | 6.00 | 5.31 |
| Fiber, % | 2.47 | 2.96 |
| Calcium, % | .88 | .80 |
| Phosphorus, % | .70 | .70 |
| ME, kcal/kg | 3300 | 3200 |
| Available Amino Acids, % | | |
| Lysine | 1.25 | 1.15 |
| Methionine | .37 | .34 |
| Threonine | .78 | .69 |
| Tryptophan | .25 | .23 |

[a]HSP 121–126 were Stage I diets. The values are weight % of total.
[b]HSP 127–132 were Stage II diets. The values are weight % of total.
[c]ASP-250 Premix provided 100 g chlorotetracycline, 100 g sulfamethazine and 50 g penicillin per ton of feed.
[d]Corn dextrose was replaced in the diet with .025, .050, .075, .100 and .125% glucan when yeast glucan was employed as an ingredient of the diet composition.
[e]Microingredients include: swine vitamin and trace mineral premix selected from the group consisting of copper sulfate, choline, selenium, vitamin E, biotin, folic acid, glycine, ethoxyquin, and mixtures thereof.

The effect of the yeast glucan is shown in Table II. During the first seven days of Stage I, increasing the level of yeast glucan resulted in a quadratic change (P<0.05) in feed intake (Table II). Pigs increased their intake in response to the increased concentration of dietary yeast glucan (from 0 to 1.0 lb of yeast glucan/ton) but adding more glucan had little effect on intake. Daily gain followed the same pattern as feed intake. Adding more yeast glucan into starter diets during the last six days of Stage I resulted in linear decreases in daily gain (P<0.02) and feed intake (P<0.05). Table II shows that excellent optimal growth and feed intake were obtained when pigs were fed with 0.5 and 1.0 pound of yeast glucan/ton of feed, respectively. Table II further shows that starter pigs fed with 0.5 pound yeast glucan/ton grew 14.3% faster and were 8.7% more feed efficient than those with no added yeast glucan. The results in Table II also demonstrate that over the last 20 days of the experiment, daily gain (P<0.07) and feed intake (P<0.05) changed quadratically as more yeast glucan was added to the diets. Optimal levels of gain and feed intake over the last growth period were found in pigs fed with 0.5 pound of yeast glucan/ton of feed. Overall, growth performance of pigs changed quadratically as more yeast glucan was added to the diet. Table II indicates that performance was greatest at the lowest inclusion level of yeast glucan (0.5 lb/ton) and declined as dietary glucan increased. The results of this experiment demonstrated that yeast glucan improved growth rate and feed intake when fed at low levels.

results shown in Table III demonstrate that addition of yeast glucan to animal feeds significantly improved the growth of weaned pigs (p<0.05). The average results of the six tests

TABLE II

Effect of Yeast Glucan Addition to Animal Feed on Growth Performance of Starter Pigs

| Glucan, lb/ton[a] | 0.0 | 0.5 | 1.0 | 1.5 | 2.0 | 2.5 |
|---|---|---|---|---|---|---|
| Glucan Intake (mg/day)[b] | 0 | 135 | 270 | 398 | 500 | 588 |
| Weights, kg | | | | | | |
| Initial | 6.82 | 6.82 | 6.78 | 6.80 | 6.78 | 6.82 |
| 7-day | 7.62 | 7.70 | 7.85 | 7.58 | 7.58 | 7.52 |
| 13-day | 9.07 | 9.35 | 9.22 | 8.95 | 8.85 | 8.63 |
| Final | 19.05 | 20.28 | 19.78 | 19.73 | 19.00 | 18.53 |
| Daily gain, kg/day | | | | | | |
| 0–7 d | .113 | .128 | .145 | .113 | .112 | .098 |
| 8–13 d[c] | .238 | .272 | .232 | .223 | .212 | .175 |
| 14–33 d[d] | .498 | .548 | .528 | .538 | .507 | .495 |
| Overall[e] | .368 | .408 | .393 | .383 | .368 | .345 |
| Daily feed, kg/day | | | | | | |
| 0–7 d[f] | .142 | .145 | .167 | .150 | .140 | .128 |
| 8–13 d[g] | .323 | .333 | .343 | .313 | .318 | .272 |
| 14–33 d[f] | .687 | .740 | .725 | .725 | .678 | .667 |
| Overall[e] | .505 | .538 | .537 | .527 | .498 | .472 |
| Feed:Gain | | | | | | |
| 0–7 d | 1.280 | 1.398 | 1.247 | 1.625 | 1.367 | .990 |
| 8–13 d | 1.367 | 1.248 | 2.137 | 1.515 | 1.545 | 1.735 |
| 14–33 d | 1.378 | 1.353 | 1.372 | 1.343 | 1.335 | 1.353 |
| Overall | 1.367 | 1.322 | 1.367 | 1.350 | 1.348 | 1.370 |

[a]Glucan product used was a commercial yeast glucan prepared from *Saccharomyces cerevisiae*.
[b]Glucan intake was calculated by multiplying the inclusion rate of yeast glucan (lb/ton) with the overall feed intake.
[c]Glucan linear effect (P<.02).
[d]Glucan quadratic effect (P<.07).
[e]Glucan quadratic effect (P<.01).
[f]Glucan quadratic effect (P<.05).
[g]Glucan linear effect (P<.05).

Example III

The effect of yeast glucan addition to animal feed was also tested with six additional randomized, complete-block experiments as described above. The animal feed compositions employed were the same as the stages I and II diets (Table I) containing 0.05 weight % of yeast glucan. The indicate that yeast glucan increased daily gain 10.5% and the pigs were 1.3 Kg heavier at the end of the tests than those pigs which were not fed with feeds containing yeast glucan. Of particular interest was that there were no difference in efficiency of feed utilization for weight gain (see also Table II), indicating that the growth improvement was due solely to the presence of yeast glucan in the feed compositions.

TABLE III

Effects of Yeast Glucan on Growth Performance of Weaned Pigs

| Swine Test Number | 92108 | 92128 | 92137 | 93108 | 93132 | 94104 | Six-Test Average |
|---|---|---|---|---|---|---|---|
| Initial weight, Kg | | | | | | | |
| Control[a] | 6.7 | 6.8 | 6.4 | 6.2 | 6.2 | 7.2 | 6.6 |
| Yeast Glucan[b] | 6.7 | 6.8 | 6.4 | 6.2 | 6.2 | 7.2 | 6.6 |
| Final weight, Kg | | | | | | | |
| Control | 18.5 | 19.1 | 19.7 | 19.7 | 19.1 | 18.4 | 19.1 |
| Yeast Glucan | 20.9 | 20.4 | 20.5 | 20.5 | 20.3 | 19.6 | 20.4 |
| Advantage | 2.4 | 1.3 | .8 | .8 | 1.2 | 1.2 | 1.3 |
| Daily gain, Kg/day | | | | | | | |
| Control | .36 | .37 | .40 | .41 | .39 | .34 | .38 |
| Yeast Glucan | .42 | .41 | .43 | .43 | .43 | .38 | .42 |

TABLE III-continued

Effects of Yeast Glucan on Growth Performance of Weaned Pigs

| Swine Test Number | 92108 | 92128 | 92137 | 93108 | 93132 | 94104 | Six-Test Average |
|---|---|---|---|---|---|---|---|
| % Over Control | 17.4 | 10.8 | 7.5 | 4.9 | 10.3 | 11.8 | 10.5 |

[a]Control - the feed composition did not contain yeast glucan.
[b]Yeast Glucan - the feed compositon contained 0.05 weight % of yeast glucan.

Example IV

This example demonstrates that the growth enhancement of starter pigs fed with animal feed compositions containing yeast glucan was not due to antibacterial or antifungal effect of the yeast glucan.

The test was carried out the same as those described in Example II except that antibiotics were deleted as noted in Table IV.

TABLE IV

Effect of Yeast Glucan Addition to Animal Feed in Medicated Starter Pig Diets[a]

| Yeast Glucan, % of diet | 0 | .10 | .10 |
|---|---|---|---|
| Medication[b] | Added | None | Added |
| Final wt, Kg[c] | 18.42 | 17.83 | 19.23 |
| Gain, Kg/day[c] | .34 | .33 | .37 |
| Feed intake, Kg/day[c] | .48 | .46 | .52 |
| Feed:Gain | 1.39 | 1.40 | 1.38 |

[a]6 pens per treatment
[b]Medication contained 110 ppm sulfamethazine, 110 ppm of chlorotetracycline, and 55 ppm pf penicillin (by weight)
[c]p<.05

Table IV shows that in the absence of medication, the weight gain decreased slightly from 0.34 Kg/day to 0.33 Kg/day, indicating medication played an important role in antibacterial or antifungal activity. When both yeast glucan and medication were included in the feed composition, the weight gain increased significantly from 0.34 Kg/day to 0.37 Kg/day, indicating that yeast glucan improved the growth rate of the animals. Table IV again shows that yeast glucan did not improve the feed efficiency, similar to those shown in Examples II and III.

Example V

This is a comparative example illustrating that a feed composition containing either autolyzed yeast or whole cell yeast did not enhance the growth of starter pigs.

The experiments were carried out as those described in Example I with the exception that yeast products as noted in Tables V and VI were included in the feed compositions shown in Table I.

TABLE V

Comparison of Yeast Glucan with Alternative Yeast Products as Additives to Animal Feed

| Additive[a] | None | Yeast Glucan | | Yeast Cell Walls[b] | | Yeast Cells[c] |
|---|---|---|---|---|---|---|
|  |  | (.05) | (.10) | (.10) | (.20) | (.75) |
| Final wt, Kg[d,e] | 19.1 | 20.0 | 20.3 | 19.1 | 18.9 | 18.7 |
| Gain, g/day[e] | 391 | 418 | 427 | 390 | 386 | 379 |
| Intake, g/day | 530 | 561 | 563 | 508 | 515 | 516 |
| Feed:Gain | 1.35 | 1.34 | 1.32 | 1.30 | 1.33 | 1.36 |

[a]The values in the parenthesis are weight % of the additives shown in total feed composition.
[b]Yeast cell walls are the insoluble cell wall fraction before yeast glucan was prepared therefrom.
[c]Commercial Baker's yeast.
[d]The initial weight was 6.2 Kg per pig.
[e]p<.05

Table V shows that simply feeding yeast cell walls or yeast cells did not improve the growth rate of animals. Wishing not to be bound by theory, it is believed that the upper digestive tract of the animals (i.e., stomach and small intestine) is not capable of removing the protein, fat, and other components of the yeast cell wall or yeast cells to expose the yeast glucan and, therefore, the animals are not capable of receiving the same benefit from yeast cell walls or yeast cells as from the yeast glucan.

TABLE VI

Effect of Addition of Yeast Products on Growth Performance of Starter Weanling Pigs Percentage Gain or Loss over Control[a]

| | MacroGard V[b] 0.025% | MacroGard V[c] 0.05% | PolarStar[d] 0.05% | Autolyzed[e] Yeast 2.50% | Autolyzed[e] Yeast 5.00% | Whole[f] Cell Yeast 5.00% |
|---|---|---|---|---|---|---|
| Weights | | | | | | |
| Initial | 0.0 | 0.0 | 0.0 | 0.0 | 0.0 | 0.0 |
| 13 day | 3.1 | 3.0 | 2.5 | −4.2 | −6.1 | 0.0 |
| Final | 6.5 | 3.6 | 12.3 | −5.5 | 2.1 | 4.5 |
| Daily Gain | | | | | | |
| Stage I | 14.3 | 9.8 | 9.5 | −14.6 | −18.1 | 1.5 |
| Stage II | 10.0 | 6.0 | 21.0 | −6.5 | 6.9 | 8.3 |
| Overall | 10.9 | 6.8 | 18.2 | −7.7 | −2.6 | 6.4 |
| Daily Feed | | | | | | |
| Stage I | 3.1 | 6.2 | 5.3 | −17.4 | −22.6 | −9.5 |
| Stage II | 7.7 | 5.5 | 14.9 | −10.4 | −5.0 | −3.3 |
| Overall | 6.5 | 6.3 | 11.9 | −11.8 | −13.3 | −4.8 |
| Feed: Gain | | | | | | |
| Stage I | 8.7 | 20.2 | 3.1 | 2.6 | −1.3 | 9.7 |
| Stage II | 1.8 | 0.4 | 5.6 | 4.0 | 11.4 | 10.3 |
| Overall | 3.3 | 0.0 | 5.0 | 3.7 | 8.8 | 10.3 |

[a]Control pigs were fed with diets (TABLE I) containing no yeast glucan or yeast products.
[b]MacroGard V was a commercial yeast glucan, both β(1–3) and β(1–6) linkages, used at an inclusion level of 0.025 weight % in the feed.
[c]The inclusion of MacroGard V yeast glucan in the feed was 0.05 weight %.
[d]PolarStar was an experimental yeast glucan, both β(1–3) and β(1–6) linkages, used at an inclusion level of 0.05 weight %.
[e]Autolyzed yeast was a commercial product obtained from *Saccharomyces cerevisiae* at an inclusion of 5.0 weight %.
[f]Whole cell yeast was commercial Baker's yeast *Saccharomyces cerevisiae* at an inclusion of 5 weight %.

As shown in Table VI, daily gain, daily feed intake and efficiency of feed utilization were decreased by the addition of autolyzed and whole cell yeast products during Stage I. Furthermore, daily gain and feed intake were less effective by inclusion of autolyzed or whole cell yeast products in Stage II and starter pigs fed either 5.0% whole cell yeast or 5.0% autolyzed yeast had better efficiency when compared with 2.50% autolyzed yeast inclusion due to the nutritional factor contributed to these feed inclusion level. Moreover, Table VI also shows that adding glucan to the diet improved daily gain and efficiency of feed utilization when compared with control.

The results shown in the above examples clearly demonstrate that the present invention is well adapted to carry out the objects and attain the end and advantages mentioned as well as those inherent therein. While modifications may be made by those skilled in the art, such modification are encompassed within the spirit of the present invention as defined by the specification and the claims.

What is claimed is:

1. A composition comprising an animal feed and a yeast glucan wherein said yeast glucan is present in said composition in an amount in the range of about 0.001 to about 10 weight percent, said amount being sufficient to effect growth rate enhancement of an animal, by at least 2% to at least 6%, which is orally administered with said composition and wherein said yeast glucan is essentially free of mannan and phosphomannan or mannoprotein and has a glucan content of beta(1–3) and beta (1–6) linkages of from about 40% to about 99%.

2. A composition according to claim 1, wherein said amount is in the range of from about 50 g to about 2,500 g of said yeast glucan per ton of said composition.

3. A composition according to claim 1, wherein said amount is in the range of from about 100 g to about 2,000 g of said yeast glucan per ton of said composition.

4. A composition according to claim 1, wherein said amount is in the range of from 200 g to 1,500 g of said yeast glucan per ton of said composition.

5. A composition according to claim 1, wherein said yeast glucan contains a mixture of β(1–3) and β(1–6) glucans in the range of from about 40 to about 90 weight %.

6. A composition according to claim 1, wherein said yeast glucan is derived from a yeast selected from the group consisting of *Saccharomyces cerevisiae, Saccharomyces uvarum, Candida utilis, Kluvveromvces fragilis, Pichia pastoris,* and mixtures thereof.

7. A composition according to claim 1, wherein said yeast glucan is derived from *Saccharomyces cerevisiae*.

8. A composition according to claim 1, wherein said yeast glucan is produced by (1) preparing a yeast suspension in an alkaline solution whereby a mixture containing insoluble yeast cell wall fraction is formed; (2) separating said insoluble yeast cell wall fraction from said mixture; (3) suspending said insoluble yeast fraction in an acid solution to form a yeast glucan; and (4) separating said yeast glucan from said acidic solution.

9. A composition according to claim 8, wherein said alkaline solution is a solution of sodium hydroxide.

10. A composition according to claim 8, wherein said yeast is *Saccharomyces cerevisiae*.

* * * * *